(12) United States Patent
Deshpande et al.

(10) Patent No.: US 8,043,324 B2
(45) Date of Patent: Oct. 25, 2011

(54) INTRAVASCULAR FILTER DEVICE WITH PIEZOELECTRIC TRANSDUCER

(75) Inventors: Abhijit Y. Deshpande, Santa Clara, CA (US); Lawrence Wasicek, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 714 days.

(21) Appl. No.: 11/929,107

(22) Filed: Oct. 30, 2007

(65) Prior Publication Data

US 2009/0112228 A1 Apr. 30, 2009

(51) Int. Cl.
*A61M 1/34* (2006.01)
*A61B 17/225* (2006.01)

(52) U.S. Cl. ......................... 606/200; 606/128

(58) Field of Classification Search ............... 606/128, 606/39, 45, 47, 48, 167, 169, 200; 604/22; 600/471; 623/1.11, 1.12, 1.23; 601/2
See application file for complete search history.

(56) References Cited

U.S. PATENT DOCUMENTS

| | | | |
|---|---|---|---|
| 5,269,291 A | 12/1993 | Carter | |
| 5,431,663 A | 7/1995 | Carter | |
| 5,609,606 A | 3/1997 | O'Boyle | |
| 5,611,807 A | 3/1997 | O'Boyle | |
| 5,928,186 A | 7/1999 | Homsma et al. | |
| 2002/0151825 A1 | 10/2002 | Rubenchik et al. | |
| 2003/0060737 A1* | 3/2003 | Brisken | 601/2 |
| 2003/0130682 A1* | 7/2003 | Broome et al. | 606/200 |

* cited by examiner

*Primary Examiner* — Amy Lang
(74) *Attorney, Agent, or Firm* — Seager, Tufte & Wickhem, LLC

(57) ABSTRACT

An intravascular filter assembly is disclosed for fragmenting a thrombotic or atherosclerotic occlusion and capturing thrombotic or atherosclerotic debris within a blood vessel. The intravascular filter assembly includes an elongate shaft and an expandable filter coupled to the distal region of the elongate shaft. One or more piezoelectric elements are secured to the elongate shaft at a location proximal of the expandable filter. A conducting wire is attached to the one or more piezoelectric elements and extends toward the proximal end of the elongate shaft. The one or more piezoelectric elements are configured to generate ultrasonic waves when subjected to an electrical voltage to fragment a thrombotic or atherosclerotic occlusion within a blood vessel.

21 Claims, 15 Drawing Sheets

INTRAVASCULAR FILTER DEVICE WITH PIEZOELECTRIC TRANSDUCER

TECHNICAL FIELD

The disclosure is directed to elongated medical devices designed to fragment and capture thrombi or plaque within a blood vessel. More particularly, the disclosure is directed to an intravascular filter device including a piezoelectric transducer capable of fragmenting and capturing thrombi or plaque in a blood vessel.

BACKGROUND

Millions of people suffer from thrombotic or atherosclerotic occlusions in blood vessels. Such occlusions restrict the blood flow through the vessel, and if left untreated, these occlusions may lead to a heart attack, or even death. A variety of available medical devices have been manufactured to treat occlusions in a blood vessel within a patient's body. For example, directional atherectomy and percutaneous translumenal coronary angioplasty (PTCA) with or without stent deployment have been found useful in treating patients with coronary occlusions, as well as occlusions of other vessels. Atherectomy uses a device which physically removes plaque by cutting, pulverizing, or shaving in atherosclerotic vessels. Angioplasty utilizes an expandable balloon on a catheter which exerts a mechanical force on the vascular wall to enlarge the luminal diameter of an occluded vessel.

Atherectomy and angioplasty techniques typically include advancing one or more elongate medical devices (e.g., atherectomy cutter or angioplasty balloon catheter) along a guidewire to the site of the occlusion and then performing a therapeutic procedure at the site of the occlusion. During such a procedure, it is often necessary to exchange one medical device for a different medical device, increasing the time required to complete the procedure. Additionally, during a catheter exchange, it may be challenging to maintain the position of the guidewire without compromising guidewire access across the occlusion. In view of the aforementioned, there is an ongoing need to provide alternative apparatus, assemblies, systems and methods of treating an occlusion within a blood vessel of a patient's body.

SUMMARY

The disclosure is directed to several alternative designs, materials and methods of manufacturing medical device structures and assemblies.

Accordingly, one illustrative embodiment is an intravascular filter assembly for fragmenting a thrombotic or atherosclerotic occlusion and capturing thrombotic or atherosclerotic debris within a blood vessel. The vascular filter assembly includes an elongate shaft and an expandable filter coupled to the distal region of the elongate shaft. The filter includes a support hoop forming a proximal mouth and a filter mesh attached to the support hoop. One or more piezoelectric elements are secured to the elongate shaft at a location proximal of the expandable filter. A conducting wire is attached to the one or more piezoelectric elements and extends toward the proximal end of the elongate shaft. The one or more piezoelectric elements are configured to generate ultrasonic waves to fragment a thrombotic or atherosclerotic occlusion within a blood vessel.

Another illustrative embodiment is an intravascular filter assembly for fragmenting a thrombotic or atherosclerotic occlusion and capturing thrombotic or atherosclerotic debris within a blood vessel. The vascular filter assembly includes a guidewire including an elongate core wire having a distal end, a proximal end, and a distal tip including a helical coil disposed at the distal end of the elongate core wire; and a filter including a filter hoop defining a proximal mouth of the filter, a filter mesh attached to the filter hoop, and at least one strut extending from the filter hoop to the elongate core wire for coupling the filter to the guidewire. A plurality of piezoelectric elements are secured to the elongate core wire at a location proximal of the filter, wherein each of the plurality of piezoelectric elements are longitudinally spaced away from an adjacent piezoelectric element. A conducting wire is connected to each of the piezoelectric elements and extends proximally along the elongate core wire from the plurality of piezoelectric elements. A length of insulating material is disposed on the elongate core wire intermediate the filter and the plurality of piezoelectric elements.

Yet another illustrative embodiment is a method of fragmenting a thrombotic or atherosclerotic occlusion and capturing thrombotic or atherosclerotic debris within a blood vessel. The method includes providing a guidewire including an elongate core wire and an expandable filter coupled to a distal region of the guidewire. The guidewire includes one or more piezoelectric elements positioned on the elongate core wire at a location proximal of the expandable filter. The guidewire is positioned in a blood vessel such that the one or more piezoelectric elements are adjacent a thrombotic or atherosclerotic occlusion within the blood vessel. The filter is then expanded at a location downstream of the thrombotic or atherosclerotic occlusion. An electrical current is transmitted along the guidewire to the one or more piezoelectric elements, generating ultrasonic waves with the piezoelectric elements. The ultrasonic waves resonating from the piezoelectric elements fragment the thrombotic or atherosclerotic occlusion within the blood vessel. Fragmented thrombotic or atherosclerotic debris is captured in the filter. At the completion of the ultrasonic fragmenting process, the intravascular filter device may be withdrawn from the blood vessel.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
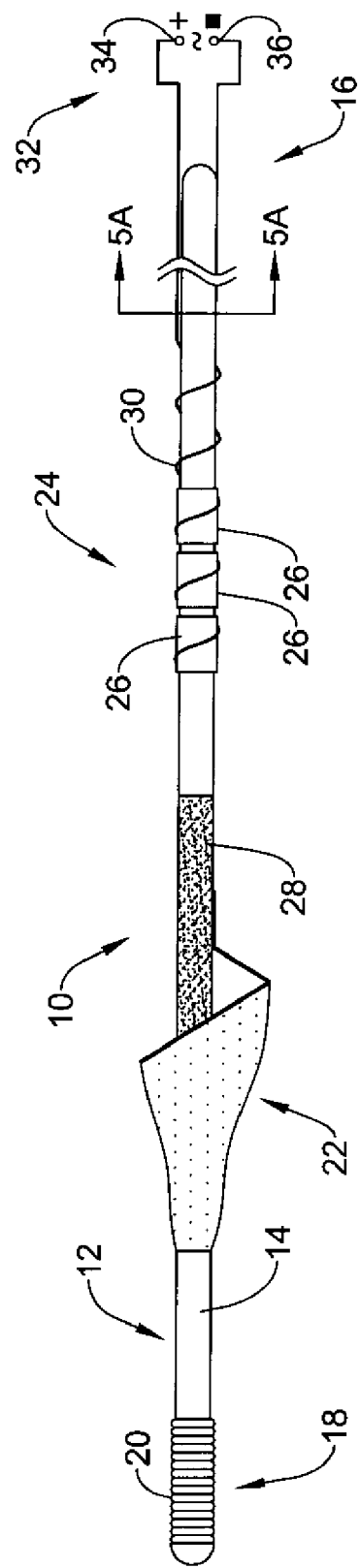
FIG. 1 is a plan view of an exemplary intravascular filter device including a piezoelectric transducer for generating ultrasonic vibrations.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

An exemplary intravascular filter device 10 is illustrated in FIG. 1. The device includes a guidewire 12 having an elongate core wire 14 extending from a proximal end 16 to a distal end 18. The distal end 18 of the guidewire 12 may include a distal tip 20, such as a helical coil, attached to the distal end of the elongate core wire 14.

The elongate core wire 14, which may have a solid cross-section or a hollow cross-section, may be made from a variety of suitable materials. In some embodiments, the elongate core wire 14 may be formed of an electrically conductive material. For example, the core wire 14 may be made from a metal, a metal alloy, or any other suitable material. Some examples of suitable metals and metal alloys include stainless steel, such as 304V, 304L, and 316LV stainless steel; mild steel; titanium or titanium alloys; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

In at least some embodiments, portions or all of the elongate core wire 14, distal tip 20 and/or other components of the guidewire 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the intravascular filter device 10 in determining its location within a blood vessel. Some examples of radiopaque materials can include, but are not limited to, gold, platinum, palladium, tantalum, tungsten alloy, polymeric material loaded with a radiopaque filler, and the like.

A filter 22, configured for capturing thrombotic or atherosclerotic fragments suspended in the blood stream, may be coupled to a distal region of the guidewire 12. Some examples of suitable filters which may be used include those disclosed in U.S. Pat. Nos. 7,094,249 and 6,245,089, the disclosures of which are incorporated herein by reference.

The intravascular filter device 10 may also include a piezoelectric transducer 24 including one or more piezoelectric elements 26 secured to the guidewire 12. The piezoelectric transducer 24 may be positioned at a location proximal of the filter 22. In some embodiments, an insulative (e.g., non-conductive) material 28 may be disposed on the outside surface of the guidewire 12 (e.g., on the outside surface of the elongate core wire 14) at a location intermediate the filter 22 and the piezoelectric transducer 24. The insulative material 28 may prevent the filter 22 from experiencing ultrasonic vibrations generated from the piezoelectric transducer 24. In some embodiments, the insulative material 28 may comprise a polymer, such as polyether block amide (PEBA), polytetrafluoroethylene (PTFE), polyamide, polyether-ester, polyurethane, polypropylene, polyethylene, or other suitable polymeric materials, or mixtures, combinations, copolymers, and the like.

A conducting wire 30 may extend distally from the proximal end 16 of the guidewire 12 to the piezoelectric transducer 24. In some embodiments, the conducting wire 30 may be formed of an electrically conducting material, such as stainless steel, gold, tungsten, titanium, or a nickel-titanium alloy, such as nitinol. As shown in FIG. 1, the conducting wire 30 may be helically wound around a length of the elongate core wire 14 of the guidewire 12. In other embodiments, the conducting wire 30 may longitudinally extend along a length of the elongate core wire 14, or extend along a length of the elongate core wire 14 in any other desired fashion.

An electronic control unit 32 may also be present for generating an electrical current to activate ultrasonic vibrations of the piezoelectric transducer 24. The electronic control unit 32, which may generate an alternating current, may include a first terminal 34 and a second terminal 36. In some embodiments, the conducting wire 30, used as a first electrode, may be electrically connected to the first terminal 34 of the electronic control unit 32. Furthermore, the elongate core wire 14, used as a second electrode, may be electrically connected to the second terminal 36 of the electronic control unit 32. Thus, an alternating electrical current may be transmitted from the electrical control unit 32 distally to the piezoelectric elements 26 of the piezoelectric transducer 24 and back to the electrical control unit 32 proximally through the electrical circuit established through the elongate core wire 14 and the conducting wire 30. Thus, the electronic control unit 32 may apply a voltage across the piezoelectric elements 26 between the outer surface of the piezoelectric elements 26 and the inner surface of the piezoelectric elements 26.

In other embodiments, instead of passing an electrical current, such as an alternating electrical current, through the elongate core wire 14, the intravascular filter device 10 may include two conducting wires extending along the guidewire 12, a first conducting wire electrically connected to the inner surface of the piezoelectric elements 26 of the piezoelectric transducer 24, and a second conducting wire connected to the outer surface of the piezoelectric elements 26 of the piezoelectric transducer 24. Thus, an alternating current may be transmitted from the electrical control unit 32 distally to the piezoelectric elements 26 of the piezoelectric transducer 24 and back to the electrical control unit 32 proximally through the electrical circuit established through the first conducting wire and the second conducting wire extending along the guidewire 12. Thus, the electronic control unit 32 may apply a voltage across the piezoelectric elements 26.

As the electrical current passes through the piezoelectric elements 26 of the piezoelectric transducer 24, a voltage forms across the piezoelectric elements 26, exciting the molecules of the piezoelectric elements 26. As the molecules are excited by the applied voltage, the dimensions of the piezoelectric elements 26 are changed. Dimensional changes in the piezoelectric elements 26 generate ultrasound waves propagating from the piezoelectric element 26. The ultrasound waves may be longitudinal waves, shear waves, or a combination of longitudinal waves and shear waves. As discussed later herein, the ultrasound waves generated by the piezoelectric elements 26 may be used to fragment plaque and/or thrombi within a blood vessel.

The electrical current, and thus the voltage, across the piezoelectric elements 26 can be varied to generate ultrasonic vibrations at a desired frequency. For example, in some embodiments it may be desirable to generate ultrasonic vibrations at a frequency of 400 kHz or less, at a frequency of 300 kHz or less, or at a frequency of 200 kHz or less. In some embodiments, ultrasonic vibrations may be generated at about 200 kHz to about 400 kHz, at about 200 kHz to about 300 kHz, at about 300 kHz to about 400 kHz, or about 350 kHz to about 400 kHz, for example. In some embodiments, ultrasonic vibrations may be generated at about 400 kHz, at about 350 kHz, at about 300 kHz, at about 250 kHz, or at about 200 kHz, for example. It is noted that the chosen material and thickness of the piezoelectric elements 26 are dependent on the desired frequency of operation. An operator may use the electrical control unit 32 to select and/or control the desired frequency of ultrasonic waves and/or the desired power generated. For example, the operator may select and/or control the frequency and/or magnitude of the electrical current transmitted to the piezoelectric elements 26 with the electrical control unit 32.

Figure 2:
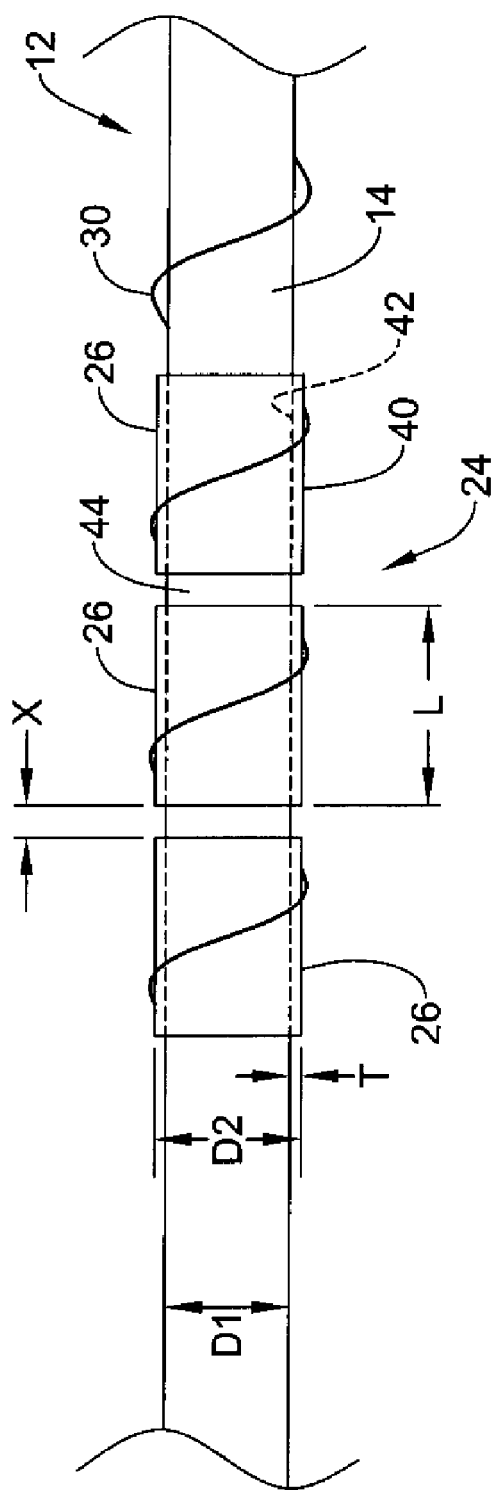
FIG. 2 is an enlarged view of a portion of the intravascular filter device of FIG. 1 showing the piezoelectric transducer.

FIG. 2 is an enlarged view of a portion of the intravascular filter device 10 further illustrating the piezoelectric elements 26 of the piezoelectric transducer 24 attached to the guidewire 12. As shown in FIG. 2, the piezoelectric transducer 24 may include three piezoelectric elements 26 secured to the elongate core wire 14 of the guidewire 12. However, in other embodiments the piezoelectric transducer 24 may include any number of piezoelectric elements 26. For example, in some embodiments the piezoelectric transducer may include one, two, four, five, six or more piezoelectric elements 26 secured to the elongate core wire 14 of the guidewire 12.

The piezoelectric elements 26 may be formed of any desired piezoelectric material. A piezoelectric material is a material having a crystalline micro-structure, such as a crystal, ceramic or polymer, which is permanently polarized such that the material will produce voltage in response to a dimension-changing mechanical force, or conversely, will undergo dimensional changes in response to an applied voltage. In this way piezoelectric materials are similar to electrostrictive materials. Some suitable piezoelectric materials include quartz, barium titanate, lead zirconate titanate (known as PZT), lead niobate, and polyvinylidene fluoride (PVDF).

The piezoelectric elements 26 may have any size, shape and/or configuration as desired. For example, as shown in FIG. 2, the piezoelectric elements 26 may be circular or annular rings extending around the circumference of the elongate core wire 14 of the guidewire 12. In other embodiments, the piezoelectric elements 26 may be strips or segments of piezoelectric material extending longitudinally, helically, circumferentially, or at another desired orientation on the elongate core wire 14. The piezoelectric elements 26 may be fixed to the elongate core wire 14 by any suitable means. For example, in some embodiments the piezoelectric elements 26 may be secured to the elongate core wire 14 with an interference fit between the inner surface of the piezoelectric elements 26 and the outer surface of the elongate core wire 14. In other embodiments, the piezoelectric elements 26 may be welded, crimped or swaged to the elongate core wire 14.

The piezoelectric elements 26 may have an outer surface 40 and an opposing inner surface 42. For instance, in embodiments in which the piezoelectric elements 26 are annular rings, the outer surface 40 may be an outer peripheral surface of the piezoelectric element 26, and the inner surface 42 may be an inner peripheral surface of the piezoelectric element 26. The inner surface 42 of the piezoelectric elements 26 may be in contact with the outer surface 44 of the elongate core wire 14, and the outer surface 40 of the piezoelectric elements 26 may be in contact with the conducting wire 30. Thus, an applied electrical voltage may be generated across the piezoelectric elements 26 between the outer surface 40 and the inner surface 42 of the piezoelectric elements 26.

The conducting wire 30 may be connected to each of the piezoelectric elements 26 as the conducting wire 30 extends distally along the guidewire 12. For instance, the conducting wire 30 may be connected to a first piezoelectric element 26 along a first helical turn of the conducting wire 30. As the conducting wire 30 extends further distally, the conducting wire 30 may be connected to a second piezoelectric element 26 along a second helical turn of the conducting wire 30. And as the conducting wire 30 extends further distally, the conducting wire 30 may be connected to a third piezoelectric element 26 along a third helical turn of the conducting wire 30, etc. The conducting wire 30 may be connected to the piezoelectric elements 26 in any desired way. For example, the conducting wire 30 may be welded (e.g., laser welding or ultrasonic welding) to the piezoelectric elements 26, or the piezoelectric elements 26 may include one or more grooves or channels in which the conducting wire 30 may be placed in or along to connect the conducting wire 30 to the piezoelectric elements 26.

In embodiments in which the piezoelectric elements 26 are annular rings, the piezoelectric elements 26 may have an inner diameter $D_1$, and outer diameter $D_2$, and a radial thickness T ($T=\frac{1}{2}(D_2-D_1)$). Thus, in embodiments when the piezoelectric elements 26 are secured to the elongate core wire 14 such that the inner surface 42 of the piezoelectric elements 26 is in contact with the outer surface 44 of the elongate core wire 14, the inner diameter $D_1$ of the piezoelectric elements 26 may be substantially equal to the outer diameter of the elongate core wire at the longitudinal location of the piezoelectric elements 26. In some embodiments the thickness T of the piezoelectric elements 26 may be about 40 to about 60 micrometers (i.e., about 0.04 millimeters to about 0.06 millimeters), or about 50 micrometers (i.e., about 0.05 millimeters). As mentioned above the ultrasonic frequency generated by the piezoelectric elements 26 may be dictated, at least in part, by the thickness T of the piezoelectric elements 26.

Each of the piezoelectric elements 26 may have a longitudinal length L of about 2 to about 6 millimeters or about 3 to about 5 millimeters. In some embodiments, the longitudinal length L of each of the piezoelectric elements 26 may be about 3 millimeters, about 4 millimeters, or about 5 millimeters, for example.

Furthermore, as shown in FIG. 2, each of the piezoelectric elements 26 may be longitudinally spaced away from an adjacent piezoelectric element 26 by a distance X. For instance, a first piezoelectric element 26 may be longitudinally spaced away from a second, adjacent piezoelectric element 26 by a distance X of about 1 to about 3 millimeters or about 1 to about 2 millimeters.

Figure 3:
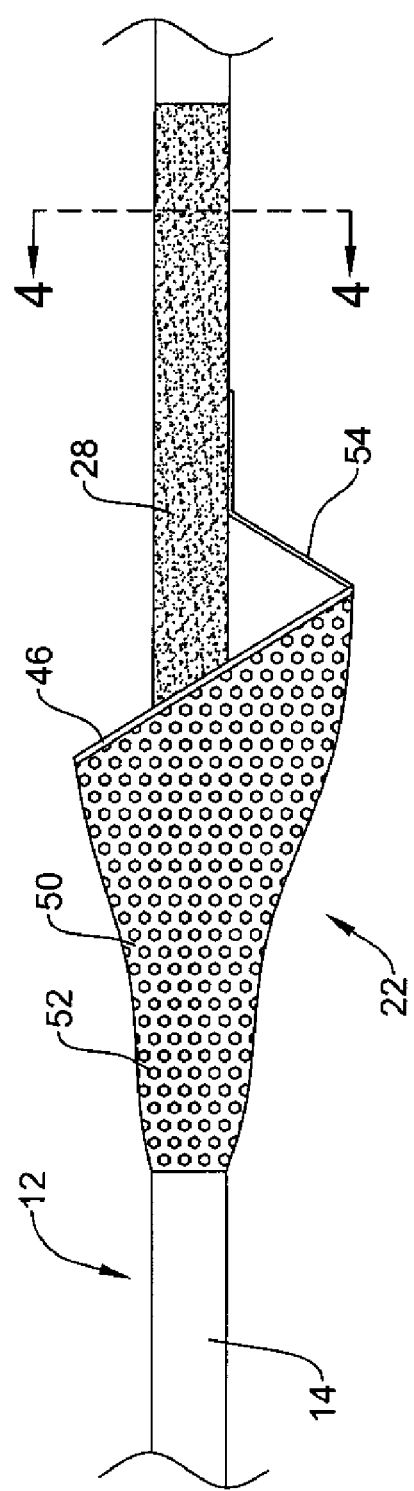
FIG. 3 is an enlarged view of a portion of the intravascular filter device of FIG. 1 showing the filter.
Figure 4:
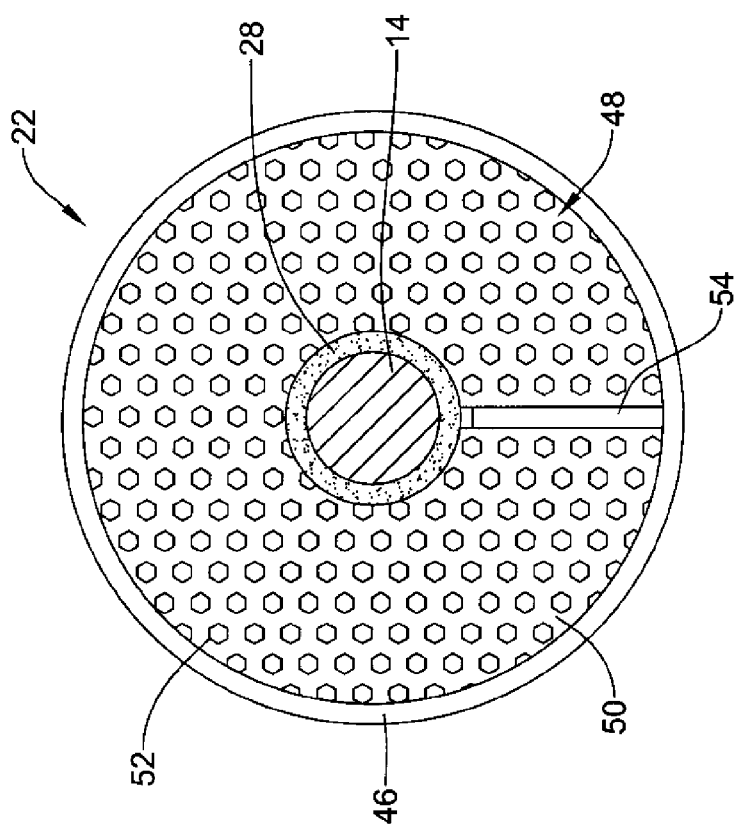
FIG. 4 is a view taken along line 4-4 of FIG. 3, looking toward the proximal mouth of the filter.

The filter 22 coupled to the guidewire 12 is further illustrated in FIGS. 3 and 4. The filter 22 may include a support hoop 46 defining a proximal mouth 48 of the filter 22. In some embodiments, the support hoop 46 may centrically encircle the guidewire 12 or the support hoop 46 may eccentrically encircle the guidewire 12. In other embodiments, the support hoop 46 may be offset such that the support hoop 46 may be directly connected to the guidewire 12. The support hoop 46 may be biased to radially expand within a blood vessel when removed from a delivery tube.

The filter 22 may also include a filter mesh 50 attached to the support hoop 46. For example, a proximal rim of the filter mesh 50 may be attached to the perimeter of the support hoop 46. In some embodiments the filter mesh 50 may include a plurality of wound, twisted, woven, interconnected, braided and/or overlapping fibers or wires. In other embodiments, the filter mesh 50 may include a microporous membrane or other suitable filtering or netting-type material. The filter mesh 50 may include a plurality of openings or pores 52 configured to allow the flow of blood therethrough, while filtering debris (e.g., thrombotic or atherosclerotic debris) suspended in the bloodstream. The distal end of the filter mesh 50 may also be attached to the guidewire 12.

The filter 22 may additionally include one or more, or a plurality of struts coupling the support hoop 46 to the guidewire 12. For example, as shown in FIGS. 3 and 4, the filter 22 may include a strut 54 extending between the support hoop 46 and the guidewire 12. As shown in FIG. 3, the strut 54 may be attached to the guidewire 12 exterior of the insulative material 28 such that any vibrations or electrical current passing through the elongate core wire 14 of the guidewire 12 will not be transmitted to the support hoop 46 and/or other components of the filter 22.

Figure 5A:
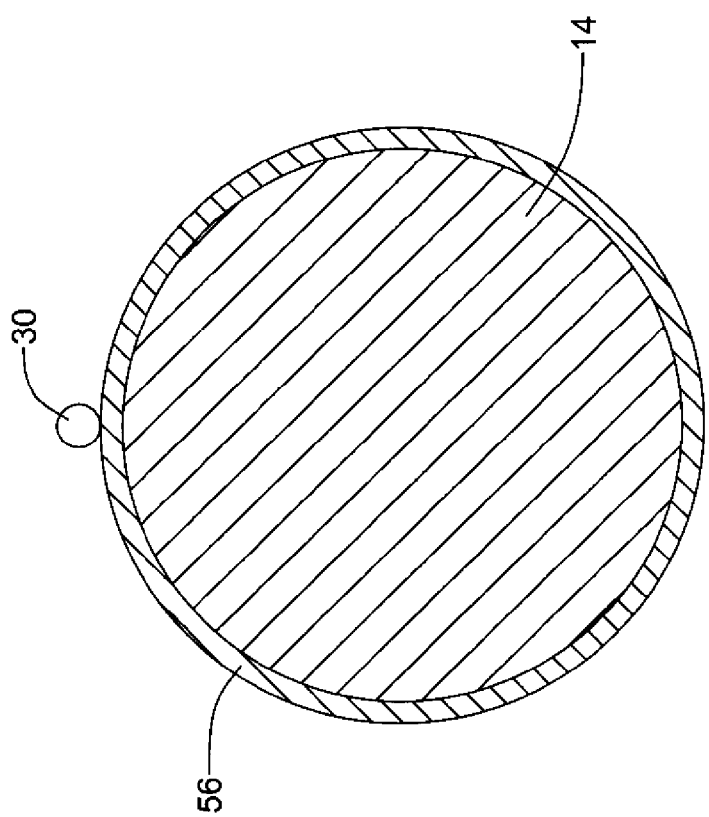
FIGS. 5A-5C are alternative cross-sectional views of the intravascular filter device of FIG. 1 taken along line 5A-5A of FIG. 1.
Figure 5B:
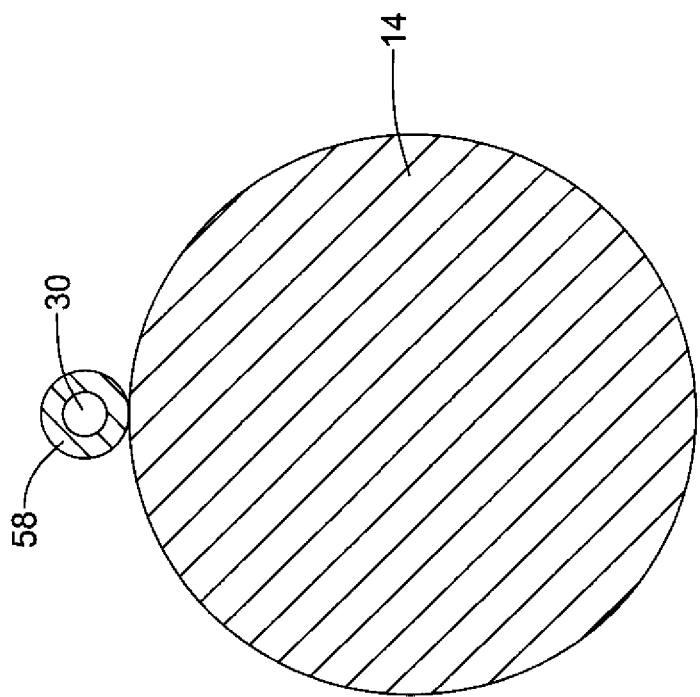
Figure 5C:
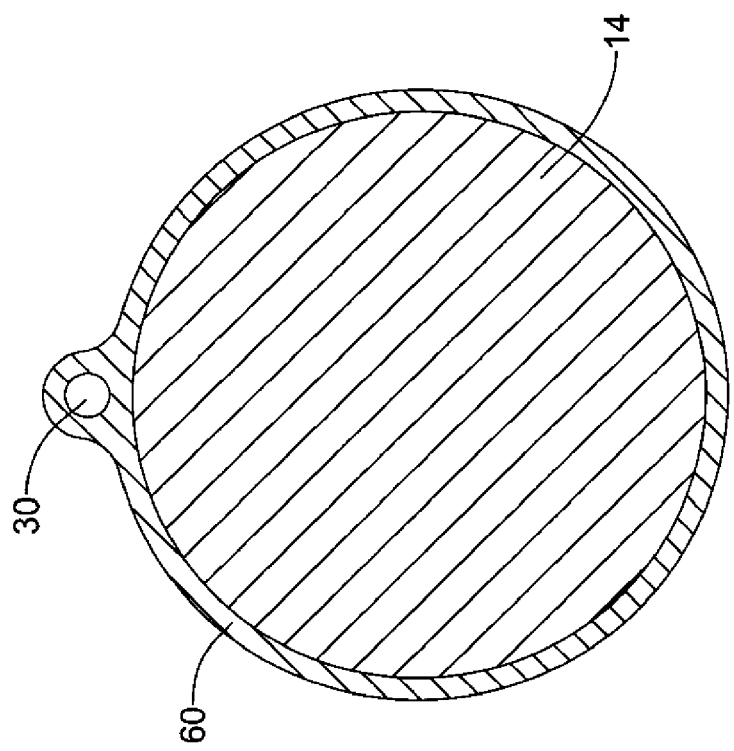

FIGS. 5A-5C are three alternative cross-sectional views taken transverse to the longitudinal axis of the guidewire 12 at a location proximal of the piezoelectric transducer 24. As shown in the figures, the conducting wire 30 is electrically insulated and/or isolated from the elongate core wire 14 of the guidewire 12. As illustrated in FIG. 5A, in some embodiments the elongate core wire 14 may be surrounded with or encased with an insulative layer 56 to insulate the elongate core wire 14 and/or isolate the elongate core wire 14 from the conducting wire 30. As illustrated in FIG. 5B, in other embodiments the conducting wire 30 may be surrounded with or encased with an insulative layer 58 to insulate conducting wire 30 and/or isolate the conducting wire 30 from the elongate core wire 14. As illustrated in FIG. 5C, in yet other embodiments the conducting wire 30 and the elongate core wire 14 may both be surround by or encased within an insulative layer 60, insulating and/or isolating the conducting wire 30 from the elongate core wire 14. Thus, an insulative layer 56, 68, 60 may be located between the elongate core wire 14 and the conducting wire 30 to prevent an electrical current from shorting across between the elongate core wire 14 and the conducting wire 30.

Figure 6:
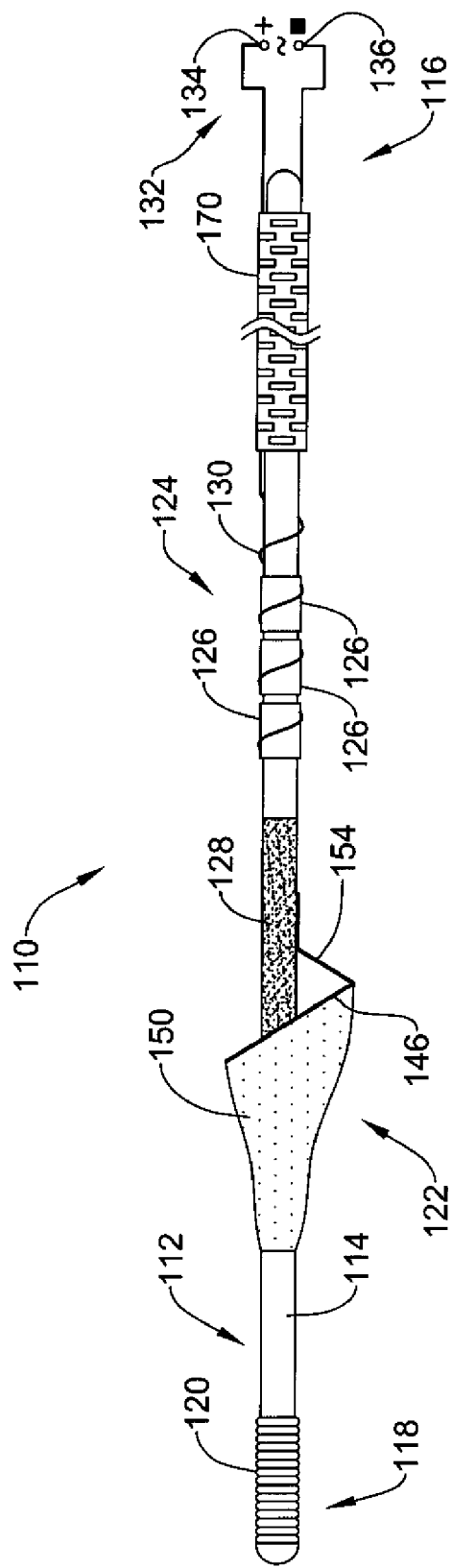
FIG. 6 is a plan view of another exemplary intravascular filter device including a piezoelectric transducer.

Another exemplary intravascular filter device 110 is illustrated in FIG. 6. The device includes a guidewire 112 having an elongate core wire 114 extending from a proximal end 116 to a distal end 118. The distal end 118 of the guidewire 112 may include a distal tip 120, such as a helical coil, attached to the distal end of the elongate core wire 114.

The elongate core wire 114, which may have a solid cross-section or a hollow cross-section, may be made from a variety of suitable materials. In some embodiments, the elongate core wire 114 may be formed of an electrically conductive material. For example, the core wire 114 may be made from a metal, a metal alloy, or any other suitable material. Some examples of suitable metals and metal alloys include those listed above regarding the elongate core wire 14. Furthermore, in at least some embodiments, portions or all of the elongate core wire 114, distal tip 120 and/or other components of the guidewire 112 may also be doped with, made oft or otherwise include a radiopaque material.

A filter 122, configured for capturing fragments suspended in the blood stream, may be coupled to a distal region of the guidewire 112. In some embodiments the filter 122 may substantially resemble the filter 22 as describe above. For instance, the filter 122 may include a support hoop 146, a filter mesh 150 attached to the support hoop 146, and at least one strut 154 coupling the support hoop 146 of the filter 122 to the guidewire 1 12. In the interest of brevity, further discussion of the filter 122 will not be reiterated.

The intravascular filter device 110 may also include a piezoelectric transducer 124 including one or more piezoelectric elements 126 secured to the guidewire 112. The piezoelectric transducer 124 is positioned at a location proximal of the filter 122. In some embodiments, an insulative (e.g., non-conductive) material 128 may be disposed on the outside surface of the guidewire 112 (e.g., on the outside surface of the elongate core wire 114) at a location intermediate the filter 122 and the piezoelectric transducer 124. The insulative material 128 may prevent the filter 122 from experiencing vibrations generated from the piezoelectric transducer 124. In some embodiments, the insulative material 128 may comprise a polymer, such as polyether block amide (PEBA), polytetraflouroethylene (PTFE), polyamide, polyether-ester, polyurethane, polypropylene, polyethylene, or other suitable polymeric materials, or mixtures, combinations, copolymers, and the like.

A conducting wire 130 may be secured to and extend proximally from the piezoelectric elements 126 of the piezoelectric transducer 124 toward the proximal end 116 of the guidewire 112. For example, the conducting wire 130 may be secured to the outer surface of each of the piezoelectric elements 126. In some embodiments, the conducting wire 130 may be formed of an electrically conducting material, such as stainless steel, gold, tungsten, titanium, or a nickel-titanium alloy, such as nitinol. As shown in FIG. 6, the conducting wire 130 may be helically wound around a length of the elongate core wire 114 of the guidewire 112. In other embodiments, the conducting wire 130 may longitudinally extend along a length of the elongate core wire 114.

An electronic control unit 132 may also be present for generating an electrical current to activate ultrasonic vibrations of the piezoelectric transducer 124. The electronic control unit 132, which may generate an alternating current, may include a first terminal 134 and a second terminal 136. In some embodiments, the conducting wire 130, used as a first electrode, may be electrically connected to the first terminal 134 of the electronic control unit 132. Furthermore, the elongate core wire 114, used as a second electrode, may be electrically connected to the second terminal 136 of the electronic control unit 132. Thus, an alternating electrical current may be transmitted from the electrical control unit 132 distally to the piezoelectric elements 126 of the piezoelectric transducer 124 and back to the electrical control unit 132 proximally through the electrical circuit established through the elongate core wire 114 and the conducting wire 130. Thus, the electronic control unit 132 may apply a voltage across the piezoelectric elements 126.

It is noted that in other embodiments, instead of passing an electrical current, such as an alternating electrical current, through the elongate core wire 114, the intravascular filter device 10 may include two conducting wires extending along the guidewire 112, a first conducting wire electrically connected to the inner surface of the piezoelectric elements 126 of the piezoelectric transducer 124, and a second conducting wire connected to the outer surface of the piezoelectric elements 126 of the piezoelectric transducer 124. Thus, an alternating current may be transmitted from the electrical control unit 132 distally to the piezoelectric elements 126 of the piezoelectric transducer 124 and back to the electrical control unit 132 proximally through the electrical circuit established through the first conducting wire and the second conducting wire extending along the guidewire 112. Thus, the electronic control unit 132 may apply a voltage across the piezoelectric elements 126.

As the electrical current passes through the piezoelectric elements 126 of the piezoelectric transducer 124, a voltage forms across the piezoelectric elements 126, exciting the molecules of the piezoelectric elements 126. As the molecules are excited by the applied voltage, the dimensions of the piezoelectric elements 126 are changed. Dimensional changes in the piezoelectric elements 126 generate ultrasound waves propagating from the piezoelectric element 126. The ultrasound waves may be longitudinal waves, shear waves, or a combination of longitudinal waves and shear waves. As discussed later herein, the ultrasound waves generated by the piezoelectric elements 126 may be used to fragment plaque and/or thrombi within a blood vessel.

The electrical current, and thus the voltage, across the piezoelectric elements 126 can be varied to generate ultrasonic vibrations at a desired frequency. For example, in some embodiments it may be desirable to generate ultrasonic vibrations at a frequency of 400 kHz or less, at a frequency of 300 kHz or less, or at a frequency of 200 kHz or less. In some embodiments, ultrasonic vibrations may be generated at about 200 kHz to about 400 kHz, at about 200 kHz to about 300 kHz, at about 300 kHz to about 400 kHz, or about 350 kHz to about 400 kHz, for example. In some embodiments, ultrasonic vibrations may be generated at about 400 kHz, at about 350 kHz, at about 300 kHz, at about 250 kHz, or at about 200 kHz, for example. It is noted that the chosen material and thickness of the piezoelectric elements 126 are dependent on the desired frequency of operation. An operator may use the electrical control unit 132 to select and/or control the desired frequency of ultrasonic waves and/or the desired power generated. For example, the operator may select and/or control the frequency and/or magnitude of the electrical current transmitted to the piezoelectric elements 126 with the electrical control unit 132.

The intravascular filter device 110 also may include a hypotube 170 extending along a proximal portion of the guidewire 112 proximal of the piezoelectric transducer 124. As may be better seen from FIG. 7, which is an enlarged view of a portion of the guidewire 112 including the hypotube 170, the hypotube 170 may be a metallic tubular member having a plurality of slots 172 cut into the wall of the metallic tubular member to impart desired flexibility characteristics to the metallic tubular member.

Figure 7:
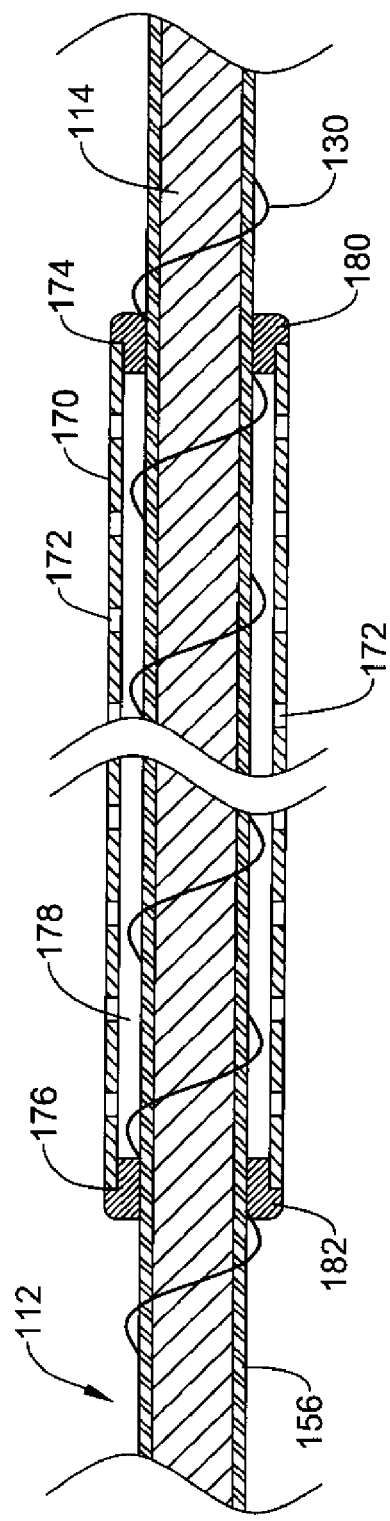
FIG. 7 is a partial cross-sectional view of a portion of the intravascular filter device of FIG. 6.

As shown in FIG. 7, the hypotube 170 may be spaced away from the elongate core wire 114 and secured in place by one or more spacers. For example, a first spacer 180 may be used to secure the proximal end 174 of the hypotube 170, and a second spacer 182 may be used to secure the distal end 176 of the of the hypotube 170. One or more additional spacers may be located at locations intermediate the proximal end 174 and the distal end 176 of the hypotube 170 to further secure the hypotube 170 in place.

The conducting wire 130 may extend through the lumen 178 of the hypotube 170, such that the conducting wire 130 is enclosed within the hypotube 170. Thus, the conducting wire 130 may be protected from contacting other structures, such as other medical devices and/or the inner surface of a blood vessel. An insulating layer 156 may separate the conducting wire 130 from the elongate core wire 114 of the guidewire 112. As shown in FIG. 7, the insulating layer 156 may be disposed around the outer surface of the elongate core wire 114. However, as discussed above, in other embodiments, the conducting wire 130 may alternatively or additionally be surrounded by an insulating layer.

Figure 8:
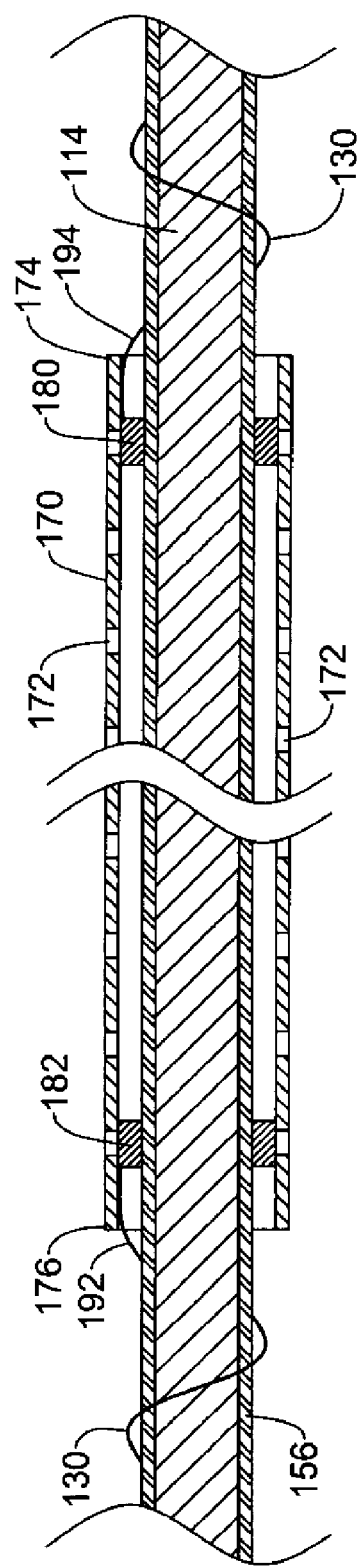
FIG. 8 is an alternative partial cross-sectional view of a portion of the intravascular filter device of FIG. 6.

An alternative embodiment of the proximal portion of the intravascular filter device 110 is illustrated in FIG. 8. The proximal portion of the intravasucular filter device 110 includes a hypotube 170 including a plurality of slots 172 formed therein to provide the hypotube 170 with desired flexibility characteristics. In this embodiment the conducting wire 130 is discontinuous, having a distal length 192 distal of the hypotube 170 and a proximal length 194 proximal of the hypotube 170. As shown in FIG. 8, the distal length 192 of the conducting wire 130 is connected to the distal end 176 of the hypotube 170 and the proximal length 194 of the conducting wire 130 is connected to the proximal end 174 of the hypotube 170. For example, the ends of the conducting wire 130 may be welded to the hypotube 170. Thus, an electrical current may pass through the hypotube 170, which may be formed of an electrically conductive material such as those disclosed above, between the proximal length 194 and the distal length 192 of the conducting wire 130. Spacers 180, 182 may be used to space the hypotube 170 from the elongate core wire 114 and/or secure the hypotube 170 in place along the guidewire 112. Additionally, an insulating layer 156 may separate the conducting wire 130 and/or the hypotube 170 from the elongate core wire 114 of the guidewire 112.

Figure 9A:
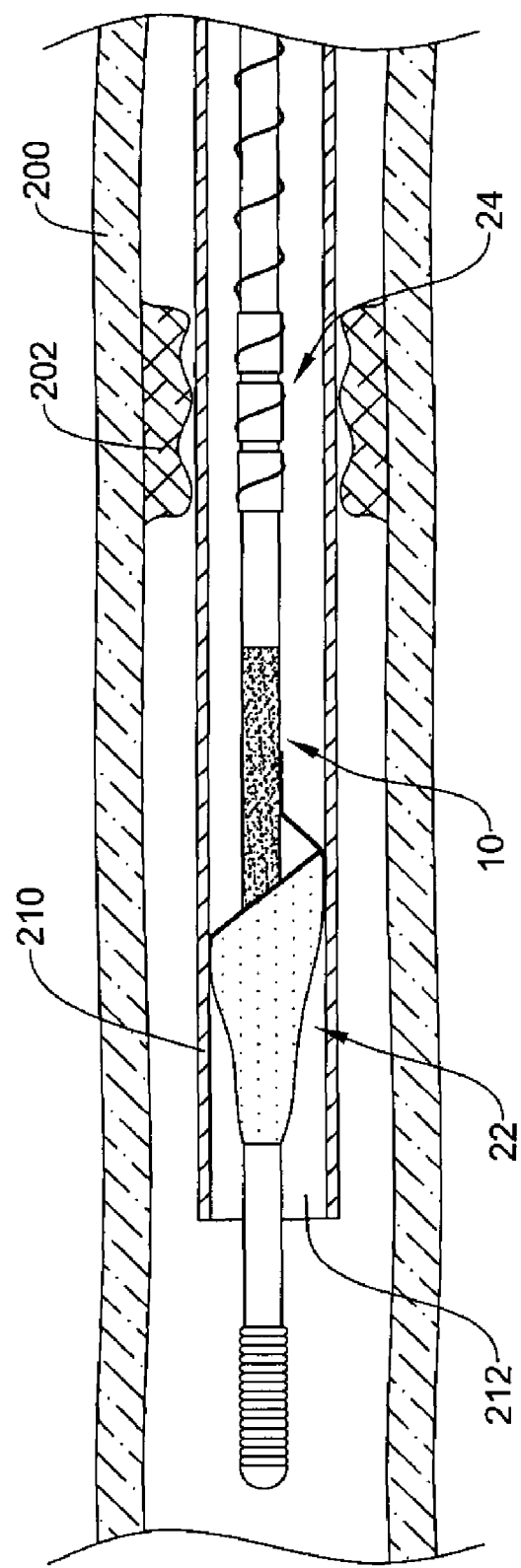
FIGS. 9A-9E illustrate an exemplary method of using an intravascular filter device including a piezoelectric transducer in the treatment of an occlusion within a blood vessel.
Figure 9B:
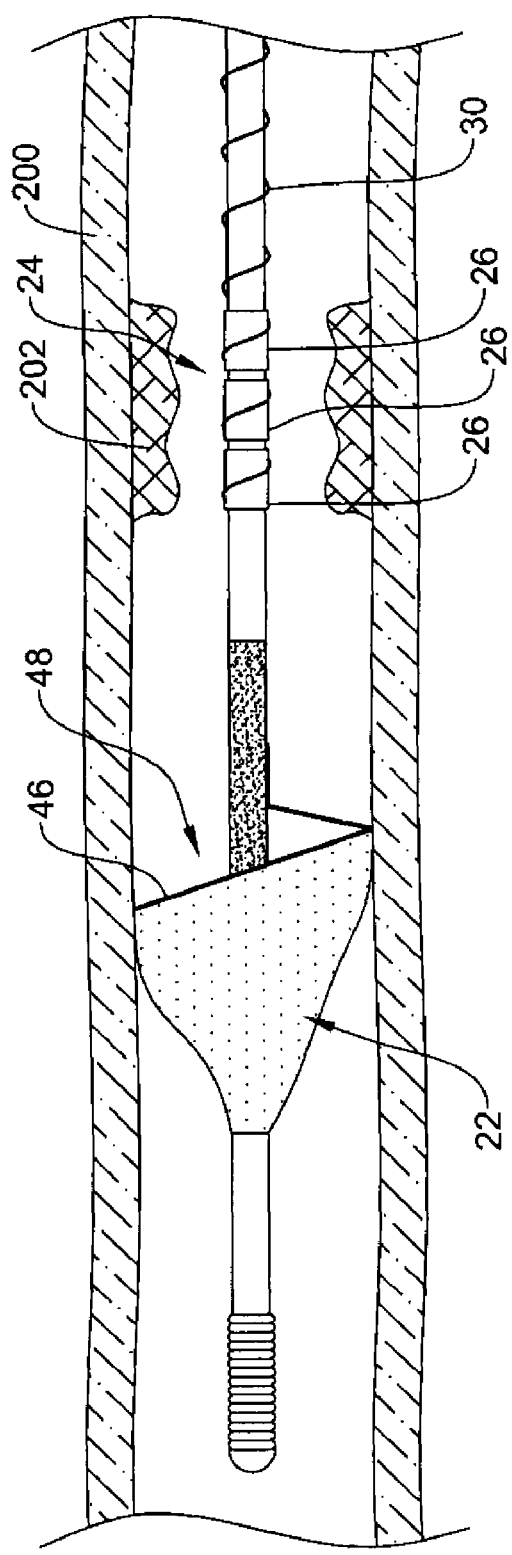

A method for fragmenting and capturing thrombi or plaque within a blood vessel using the intravascular filter device 10 will now be illustrated in FIGS. 9A-9E. As shown in FIG. 9A, the intravascular filter device 10 may be initially advanced through a blood vessel 200 within a delivery sheath 210. The filter 22 may be delivered in a collapsed configuration within the lumen 212 of the delivery sheath 210. The delivery sheath 210, with the intravascular filter device 10 disposed within the lumen 212 of the delivery sheath 210, may be advanced through the blood vessel 200 until the piezoelectric transducer 24 of the intravascular filter device 10 is positioned adjacent an occlusion 202, such as an thrombotic or atherosclerotic occlusion, on the interior wall of the blood vessel 200. With the piezoelectric transducer 24 positioned adjacent the occlusion 202, the filter 22 coupled to the guidewire 12 distal of the piezoelectric transducer 24 is located at a location distal of the occlusion 202.

Once the piezoelectric transducer 24 is positioned adjacent the occlusion 202, the delivery sheath 210 may be withdrawn proximally, allowing the filter 22 to expand into a deployed configuration as shown in FIG. 91B. In the deployed configuration, the support hoop 46 of the filter 22 may substantially extend across the lumen of the blood vessel 200 with the proximal mouth 48 facing the occlusion 202. With the filter 22 deployed, the piezoelectric elements 26 of the piezoelectric transducer 24 may remain positioned adjacent the occlusion 202. Thus, in some embodiments, the filter 22 may be expanded into the deployed configuration subsequent to positioning the piezoelectric elements adjacent the occlusion 202.

An electrical current (e.g. an alternating electrical current) may then be transmitted along the guidewire 12 to the piezoelectric elements 26 from the electronic control unit 32 (not shown) to activate the piezoelectric transducer 24. For example, an electrical pathway may be formed extending from the electronic control unit 32 distally along the conducting wire 30, across the piezoelectric elements 26, and proximal along the elongate core wire 14 back to the electronic control unit 32.

Voltage across the piezoelectric elements 26 excites the piezoelectric elements 26, generating ultrasonic waves 220 resonating from the piezoelectric elements 26. In some embodiments, the ultrasonic waves 220 generated by the piezoelectric elements 26 by the vibrations of the piezoelectric elements 26 may be longitudinal waves, shear waves, or a combination of longitudinal and shear waves. The frequency of the ultrasonic waves 220 may be controlled by adjusting the voltage across the piezoelectric elements 26 as desired. For example, the electrical current, and thus the voltage, across the piezoelectric elements 26 can be varied to generate ultrasonic waves 220 at a desired frequency. For instance, in some embodiments it may be desirable to generate ultrasonic waves 220 at a frequency of 400 kHz or less, at a frequency of 300 kHz or less, or at a frequency of 200 kHz or less. In some embodiments, ultrasonic waves 220 may be generated at about 200 kHz to about 400 kHz, at about 200 kHz to about 300 kHz, at about 300 kHz to about 400 kHz, or about 350 kHz to about 400 kHz, for example. In some embodiments, ultrasonic waves 220 may be generated at about 400 kHz, at about 350 kHz, at about 300 kHz, at about 250 kHz, or at about 200 kHz, for example. An operator may use the electrical control unit 32 to select and/or control the desired frequency of ultrasonic waves 220 and/or the desired power generated. For example, the operator may select and/or control the frequency and/or magnitude of the electrical current transmitted to the piezoelectric elements 26 with the electrical control unit 32.

Figure 9C:
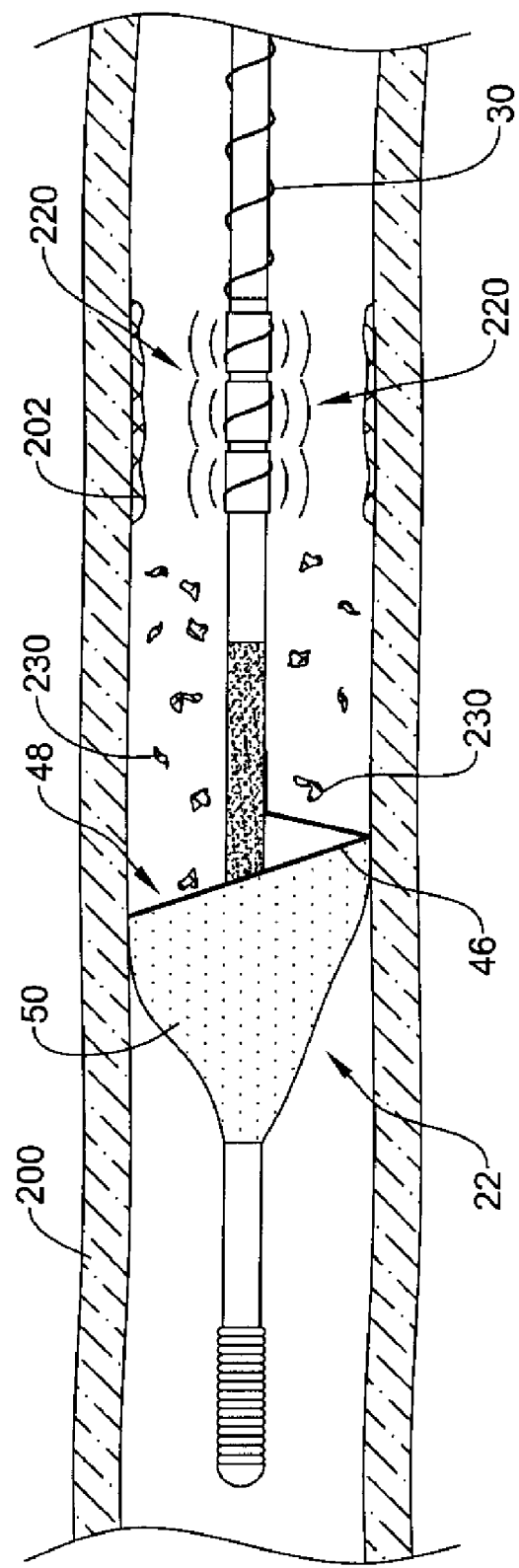

As shown in FIG. 9C, the ultrasonic waves 220 propagate toward the occlusion 202, fragmenting the tissue (e.g., plaque and/or thrombi) forming the occlusion 202 into small fragments 230 of debris. The thrombotic or atherosclerotic fragments 230 broken away from the vessel wall 200 are suspended in the bloodstream and float downstream. The filter 22, positioned downstream (e.g., distal) of the occlusion 202, extends across the vessel 200 to capture the fragments 230 suspended in the bloodstream. Fragments 230 enter the filter 22 through the proximal mouth 48 defined by the support hoop 46 of the filter 22 and are retained by the filter mesh 50, while allowing blood to flow through.

Figure 9D:
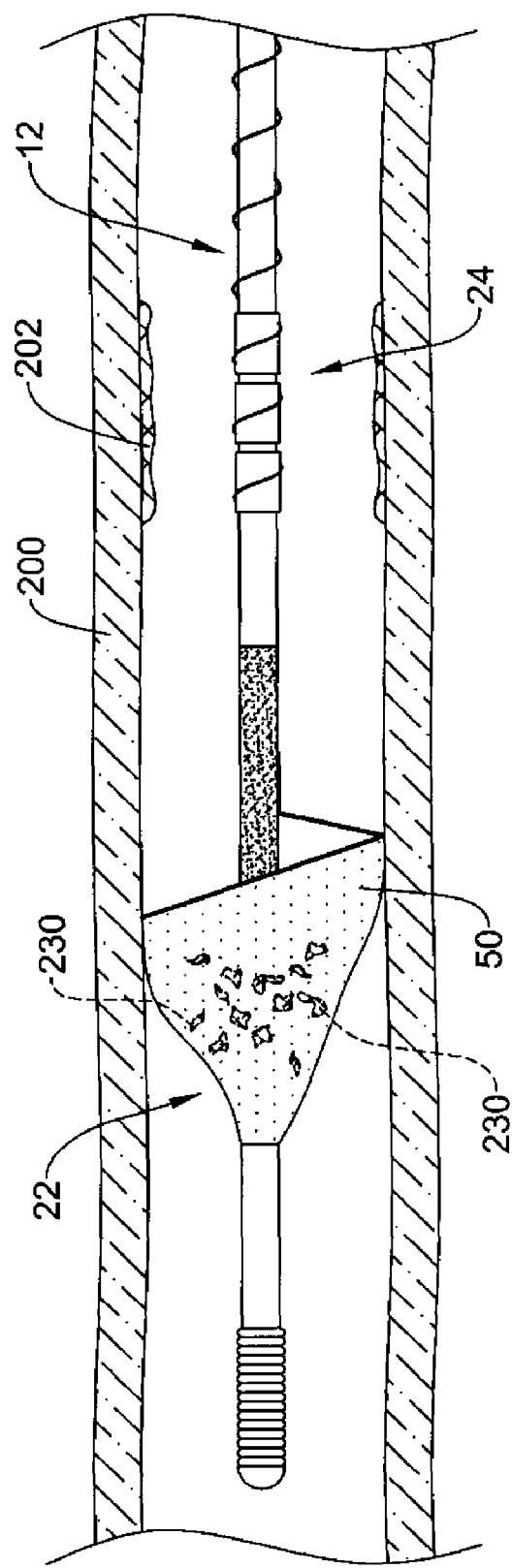
Figure 9E:
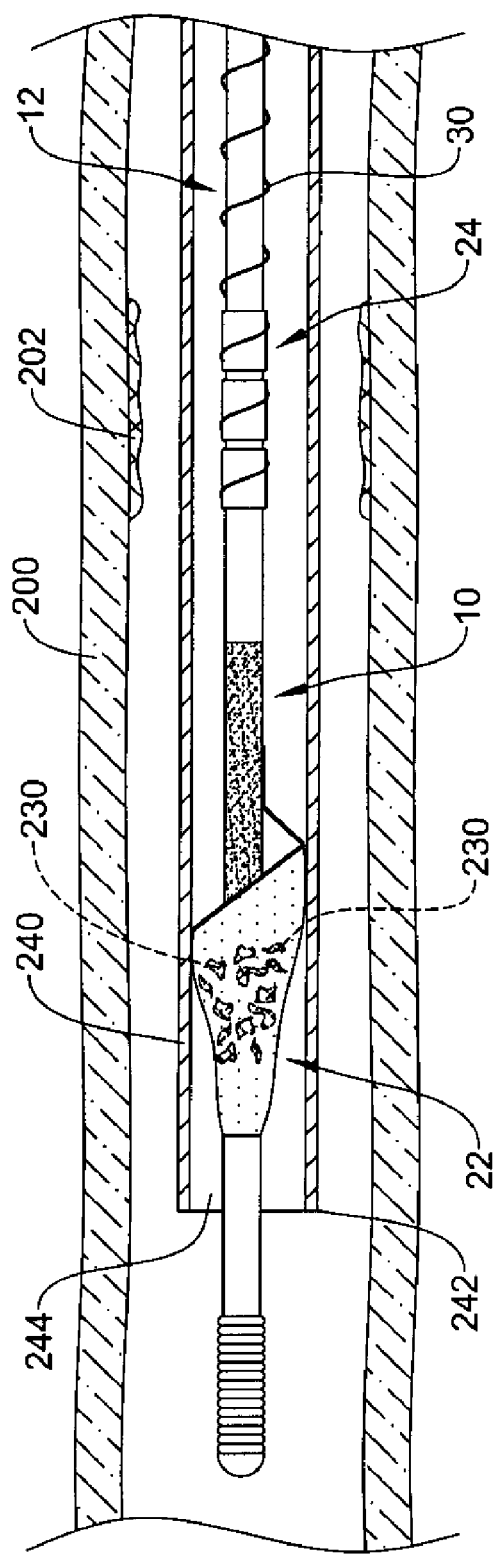

As shown in FIG. 9D, ultrasonic waves generated from vibrations of the piezoelectric elements 26 reduce and/or eliminate the occlusion 202 in the blood vessel 200, thus reducing any restrictions of blood flow through the lumen of the blood vessel 200. The filter 22, containing captured fragments 230 of debris (e.g., thrombotic or atherosclerotic debris) from the occlusion 202, prevents fragments 230 from flowing to other regions of the vasculature, such as the heart, lungs and/or brain of the patient.

After completing the application of ultrasonic vibrations waves in which the fragments 230 are captured in the filter 22, a retrieval sheath 240 may be advanced distally over the guidewire 12. The distal end 242 of the retrieval sheath 240 may be passed distally over at least a portion of the filter 22, such that the filter 22 is at least partially collapsed within the lumen 244 of the retrieval sheath 240. Thus, the collapsed filter 22, including the captured thrombotic or atherosclerotic fragments 230, and the piezoelectric transducer 24 disposed on the guidewire 12 may be retained within the lumen 244 of the retrieval sheath 240. The intravascular filter device 10 may then be withdrawn from the blood vessel 200 at the completion of the medical procedure.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An intravascular filter assembly for fragmenting a thrombotic or atherosclerotic occlusion and capturing thrombotic or atherosclerotic debris within a blood vessel, the vascular filter assembly comprising:
    an elongate shaft having a distal end, a proximal end, a distal region and a proximal region;
    an expandable filter coupled to the distal region of the elongate shaft, the filter including a support hoop forming a proximal mouth and a filter mesh attached to the support hoop;
    one or more piezoelectric elements secured to the elongate shaft at a location proximal of the expandable filter; and
    a conducting wire attached to the one or more piezoelectric elements and extending toward the proximal end of the elongate shaft;
    wherein the one or more piezoelectric elements are configured to generate ultrasonic waves to fragment a thrombotic or atherosclerotic occlusion within a blood vessel.

2. The intravascular filter assembly of claim 1, wherein the elongate shaft and the conducting wire act as an electrical pathway to provide an electrical voltage across the one or more piezoelectric elements.

3. The intravascular filter assembly of claim 1, wherein the one or more piezoelectric elements include a plurality of annular rings spaced apart along a length of the elongate shaft.

4. The intravascular filter assembly of claim 3, wherein each of the annular rings has radial thickness of about 50 micrometers.

5. The intravascular filter assembly of claim 3, wherein each of the annular rings has a longitudinal length of about 3 millimeters.

6. The intravascular filter assembly of claim 3, wherein each of the annular rings is spaced from an adjacent ring by about 1 to 2 millimeters.

7. The intravascular filter assembly of claim 3, wherein the plurality of annular rings are held in place on the elongate shaft by an interference fit.

8. The intravascular filter assembly of claim 1, further comprising an electronic control unit for controlling the power or frequency of ultrasonic waves generated by the one or more piezoelectric elements.

9. The intravascular filter assembly of claim 8, wherein the proximal region of the elongate shaft is electrically connected to the electronic control unit.

10. The intravascular filter assembly of claim 8, wherein the conducting wire is electrically connected to the electronic control unit.

11. The intravascular filter assembly of claim 1, further comprising an insulating material disposed on the elongate shaft intermediate the filter and the one or more piezoelectric elements.

12. An intravascular filter assembly for fragmenting a thrombotic or atherosclerotic occlusion and capturing thrombotic or atherosclerotic debris within a blood vessel, the vascular filter assembly comprising:
- a guidewire including an elongate core wire having a distal end, a proximal end, and a distal tip including a helical coil disposed at the distal end of the elongate core wire;
- a filter including:
    i) a filter hoop defining a proximal mouth of the filter;
    ii) a filter mesh attached to the filter hoop; and
    iii) at least one strut extending from the filter hoop to the elongate core wire for coupling the filter to the guidewire;
- a plurality of piezoelectric elements secured to the elongate core wire at a location proximal of the filter, wherein each of the plurality of piezoelectric elements are longitudinally spaced away from an adjacent piezoelectric element;
- a conducting wire connected to each of the piezoelectric elements and extending proximally along the elongate core wire from the plurality of piezoelectric elements; and
- a length of insulating material disposed on the elongate core wire intermediate the filter and the plurality of piezoelectric elements.

13. The intravascular filter assembly of claim 12, wherein each of the piezoelectric elements is an annular ring extending around the circumference of the elongate core wire.

14. The intravascular filter assembly of claim 13, wherein each of the annular rings has a radial thickness of about 0.05 millimeters.

15. The intravascular filter assembly of claim 13, wherein each of the annular rings has a longitudinal length of about 3 to 5 millimeters.

16. The intravascular filter assembly of claim 12, wherein each of the annular rings is spaced from an adjacent annular ring by a distance of about 1 to 2 millimeters.

17. The intravascular filter assembly of claim 12, further comprising an electronic control unit, wherein the conducting wire is electrically connected to a first terminal of the electronic control unit and the elongate core wire is electrically connected to a second terminal of the electronic control unit.

18. The intravascular filter assembly of claim 12, further comprising a metallic hypotube extending over a portion of the elongate core wire.

19. The intravascular filter assembly of claim 18, wherein the conducting wire extends through the metallic hypotube.

20. The intravascular filter assembly of claim 18, wherein the metallic hypotube has a proximal end and a distal end, wherein a first length of the conducting wire is secured to the distal end of the hypotube.

21. The intravascular filter assembly of claim 20, further comprising a second length of the conducting wire secured to the proximal end of the hypotube.

* * * * *